(12) United States Patent
Keles et al.

(10) Patent No.: US 7,121,824 B2
(45) Date of Patent: Oct. 17, 2006

(54) PROTRACTION HEADGEAR

(75) Inventors: Ahmet Ozlem Keles, Istanbul (TR); Brian Willison, Tonawanda, NY (US)

(73) Assignee: Great Lakes Orthodontics, Ltd., Tonawanda, NY (US)

(*) Notice: Subject to any disclaimer, the term of this patent is extended or adjusted under 35 U.S.C. 154(b) by 0 days.

(21) Appl. No.: 10/835,124

(22) Filed: Apr. 29, 2004

(65) Prior Publication Data

US 2005/0244769 A1 Nov. 3, 2005

(51) Int. Cl.
*A61C 7/00* (2006.01)
(52) U.S. Cl. .......................................... 433/5
(58) Field of Classification Search ................ 433/5, 433/69; 602/17; 24/318; 482/11
See application file for complete search history.

(56) References Cited

U.S. PATENT DOCUMENTS

| | | | | |
|---|---|---|---|---|
| 4,034,474 A * | 7/1977 | Lee | ................ | 433/69 |
| 4,328,620 A * | 5/1982 | Mack et al. | ................ | 33/514 |
| 4,368,039 A * | 1/1983 | Armstrong | ................ | 433/5 |
| 4,600,382 A * | 7/1986 | Forster | ................ | 433/5 |
| 4,988,291 A * | 1/1991 | Grummons | ................ | 433/5 |
| 5,158,451 A * | 10/1992 | Pourcho | ................ | 433/5 |
| 5,203,694 A * | 4/1993 | Klein | ................ | 433/5 |
| 5,558,090 A * | 9/1996 | James | ................ | 128/207.18 |
| 5,657,491 A * | 8/1997 | Young | ................ | 2/195.2 |
| 5,704,784 A * | 1/1998 | Wolk | ................ | 433/5 |
| 5,724,746 A * | 3/1998 | Mack | ................ | 33/514 |
| 5,790,228 A * | 8/1998 | Bell, III | ................ | 351/118 |
| 6,520,182 B1* | 2/2003 | Gunaratnam | ................ | 128/206.27 |
| 2004/0060561 A1* | 4/2004 | Kwok et al. | ................ | 128/207.11 |

* cited by examiner

Primary Examiner—Cary E. O'Connor
(74) *Attorney, Agent, or Firm*—Hodgson Russ LLP

(57) ABSTRACT

A facebow which overcomes the adverse effects and limitations of current designs by rotating the maxilla in a downward and forward direction, which assists in correcting anterior open bites. This is accomplished by a design that produces forces above the center of resistance of the maxilla and parallel to the Frankfurt horizontal plane. The extra-oral headgear design is characterized by providing two independent adjustments (forehead width and horizontal/vertical dimensions) that allow the appliance to be customized to each patient. In particular, the two independent adjustments are provided by a fully adjustable forehead pad and bilateral adjustable blocks on opposite sides of the facebow extra-oral frame to provide horizontal and vertical adjustments.

20 Claims, 4 Drawing Sheets

PROTRACTION HEADGEAR

BACKGROUND OF THE INVENTION

This invention relates to the art of orthodontic appliances for applying protraction forces, and more particularly to a new and improved orthodontic appliance and method for treatment of Class III malocclusions (underbite) characterized by the lower teeth positioned anterior to or in front of the upper teeth when in centric occlusion.

The etiology involved in Class III malocclusions can range from a dental condition to a more severe skeletal malrelationship. In the Class III dental malocclusion, teeth are tipped towards the underbite position with normal maxillary and mandibular relationships. In skeletal malocclusion, the size or relative position of the maxilla and mandible varies. For example, the maxilla can be positioned posterior to an ideally positioned mandible. In another cases, the mandible is positioned anterior to an ideally positioned maxilla. Also, combinations of the previous examples are possible.

Treatment of a Class III malocclusion, characterized by open bite pattern, is difficult since such malocclusions result from many etiological factors. Skeletal open bite cases are usually associated with an increase in the vertical growth of the maxillary posterior dentoalveolar segments. The application of conventional reverse headgear, with the associated application of mesially directed force (below the center of resistance of maxillary dentition) tends to increase the anterior open bite. The intrusion of posterior teeth becomes more difficult with age, as mechanical treatment options are limited in adult patients. Orthognathic surgery may be indicated in adult patients with severe open bite and Class III skeletal patterns with retrognathic maxilla. Previous studies have shown the effects of protraction forces on the maxillary to be complex.

Used since the 1960s, commercially available reverse pull headgear designs typically have a metal or acrylic intra-oral portion attached to teeth, and an extra-oral portion that rests against the front of the face. These two components are attached with elastic bands that exert from 300 to 800 gram centimeters on the right and left sides. The direction of elastic traction is downward and forward at the level of the lips and not parallel to the Frankfurt horizontal plane. This produces a counter clockwise or upward and forward rotation of the maxilla while protracting. This rotation opens the bite, which is an undesirable side effect for certain dental relationships and facial types.

The most important factors to be considered in maxillary protraction are the point of force application and the direction of the force. Since the mandible is attached to the temporomandibular joint (TMJ), it is impossible to achieve a stable counterbalance force in reverse pull headgear by anchorage to the chin (due to movement of the mandible). Another drawback to using the chin to stabilize is the unknown effect orthopedic forces have on the TMJ and mandibular growth. In growing children, force application to the chin by reverse-pull headgear causes downward and backward rotation of mandible. Although the retrusive forces being applied by the chin cap can benefit a prognathic mandible, it may be detrimental to the TMJ as well as increase open bite tendencies.

The appliance and method of this invention distinguishes from conventional facemasks in avoiding upward rotation of the maxilla during protraction, and the invention is characterized by providing two independent adjustments that allow the invention to be customized to each patient.

SUMMARY OF THE INVENTION

This new facebow design according to the invention overcomes the adverse effects and limitations of current designs by rotating the maxilla in a downward and forward direction, which assists in correcting anterior open bites. This is accomplished using a design that produces forces above the center of resistance of the maxilla and parallel to the Frankfort horizontal plane. The facebow includes a forehead rest, an intra-oral frame adapted to be connected to the patient's teeth and an extra-oral frame connected at one end to the intra-oral frame and connected at the other end via elastic means to the forehead rest. The extra-oral headgear design of the invention is characterized by providing two independent adjustments (forehead width and horizontal/vertical dimensions) that allow the invention to be customized to each patient. In particular the two independent adjustments are provided by a fully adjustable forehead pad and bilateral adjustable blocks on opposite sides of the facebow extra-oral frame to provide horizontal and vertical adjustments.

DETAILED DESCRIPTION OF THE INVENTION

Figure 1:
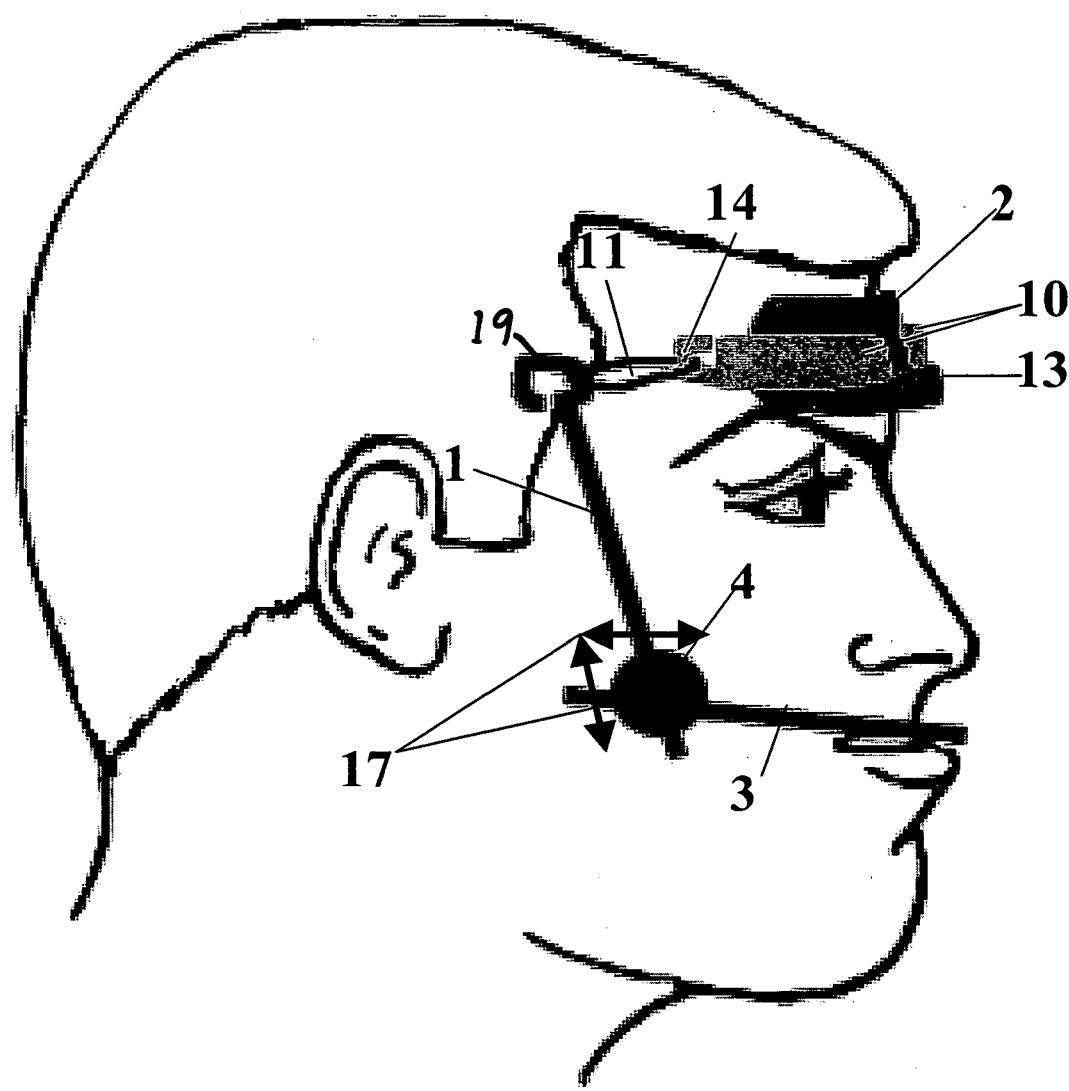
FIG. 1 is a side elevational view showing the extra-oral portion of the invention, as well as illustrating the two directions of adjustment (17)

Referring to FIG. 1, the extra-oral wire framework consists of two main parts, the generally vertical bar (1) with distal hooks (19) that attaches to the forehead rest (2) via elastic elements (11), and a front generally horizontal bar (3). The appliance includes two vertical bars (1), one on each side of the patient's head. The bars (1 and 3) are adjustably fixed by adjustment blocks (4) that provide customization to each patient. A pair of set screws (18), one pair in each block (4), are used to fix the location of the vertical and horizontal bars. In particular, one set screw (18) of each pair allows for the horizontal adjustment and the other set screw (18) of each pair allows for the generally vertical adjustment. The directions of the horizontal and vertical adjustments provided by each block (4) and set screw (18) combination are indicated by arrows (17) in FIG. 1.

Figure 2:
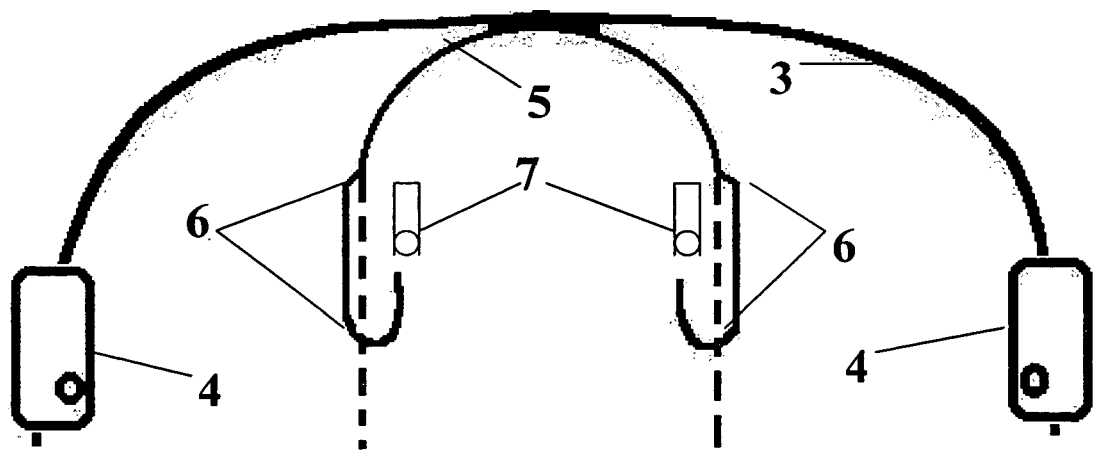
FIG. 2 is a diagrammatic top view of the intra-oral component showing the direction of attachment to the tubes (7)
Figure 3:
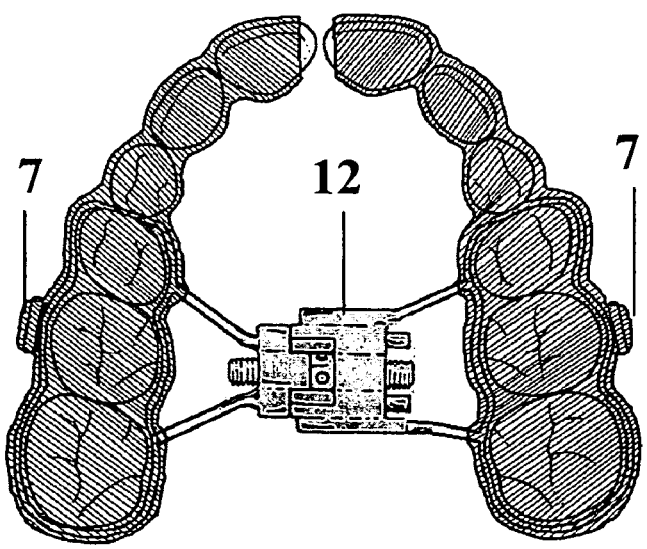
FIG. 3 is a plan view showing a recommended intra-oral appliance used to attach the intra-oral component to the teeth.

Intra-orally, the device is adapted for connection to the teeth via an acrylic splint type (rapid maxillary expander—RME) appliance (12) shown in FIG. 3 and well-known to those skilled in the art. A "U" shaped intra-oral bow (5)

shown in FIG. 2 is connected to the front horizontal bar (3) that is positioned in front of the patient's lips. The intra-oral portion of the facebow (6) is bent by the clinician to insert through the distal end of tubes (7) on right and left sides of the acrylic splint (12). The foregoing arrangement and procedure is well-known to those skilled in the art.

Figure 4A:
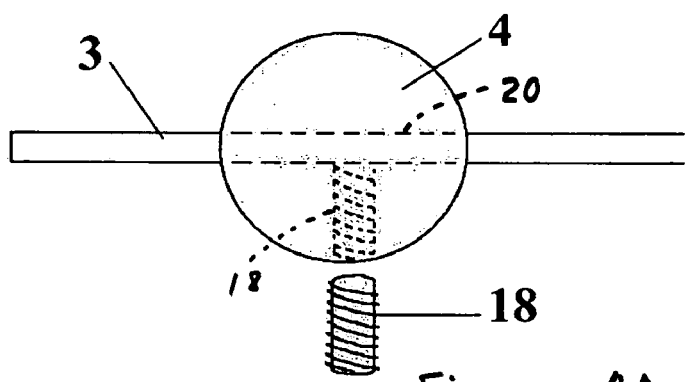
FIGS. 4A and 4B are fragmentary diagrammatic views showing the means for adjusting the horizontal (1) and vertical (3) elements of the facebow.
Figure 4B:
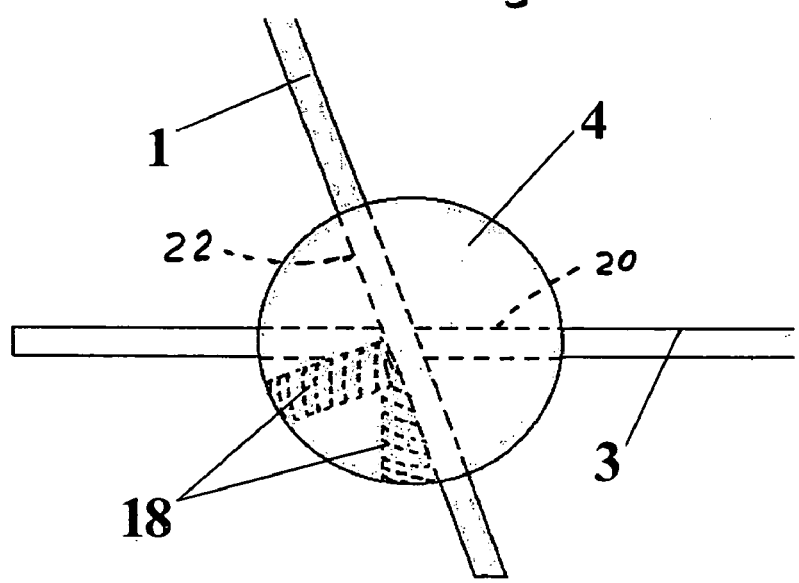

FIGS. 4A and 4B further illustrate the manner in which the front horizontal bar (3) and the generally vertical bars (1) of the extra-oral framework are adjustable. As shown in FIG. 4A, the horizontal bar or wire (3) extends through a first bore or aperture (20) in block (4). The relative cross-sectional dimensions, for example diameters, of bar (3) and bore (20) are such that bar (3) is slidably moveable within block (4). A first set screw (18) shown in FIG. 4A is threaded in block (4) to lock bar (3) in a desired position within block (4) in a known manner. This arrangement is provided for both blocks (4) and bars (3) on opposite sides of the appliance adjacent opposite sides of the patient's head.

Similarly, the generally vertical bar or wire (1) extends through a second bore or aperture (22) in block (4). Although each bar (1) is referred to as extending generally vertically, in a typical appliance such as the one shown herein, each bar (1) is disposed at a relatively large acute angle with respect to the axis of the generally horizontal bar (3). The relative cross-sectional dimensions, for example diameters, of bar (1) and bore (22) are such that bar (1) is slidably moveable within block (4). A second set screw (18) shown in FIG. 4B is threaded in block (4) to lock bar (1) in a desired position within block (4) in a known manner. This arrangement also is provided for both blocks (4) and bars (1) on opposite sides of the appliance adjacent opposite sides of the patient's head.

Figure 5:
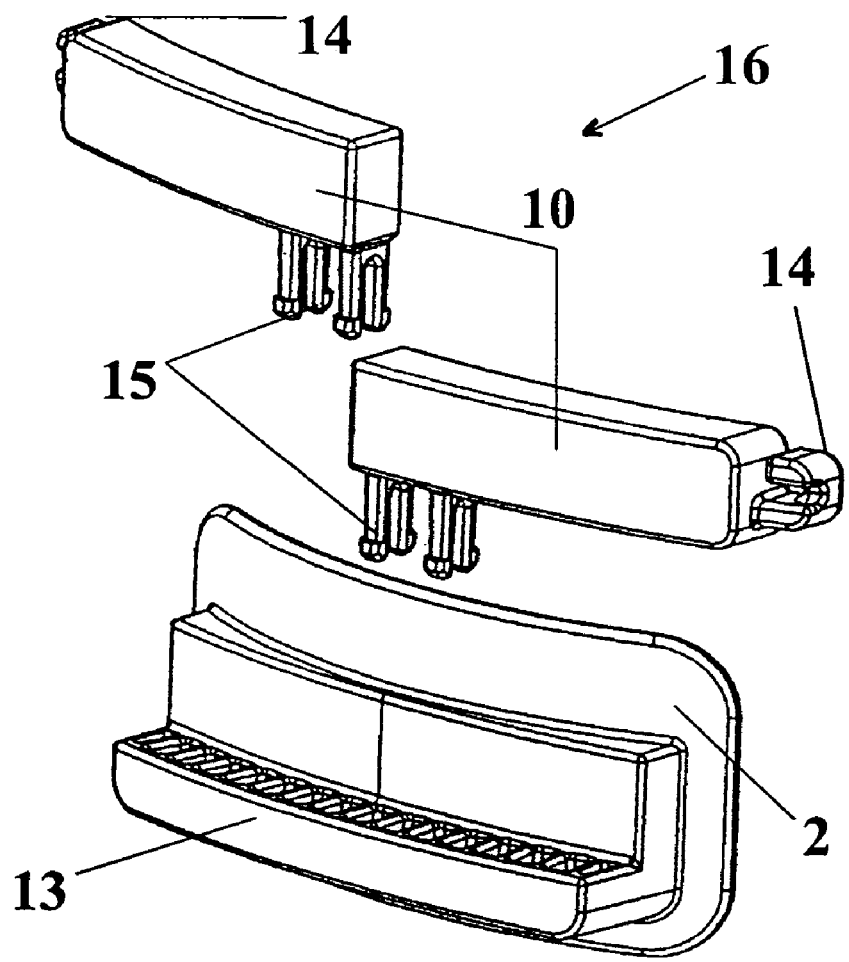
FIG. 5 is an exploded perspective view of the forehead pad assembly.
Figure 6:
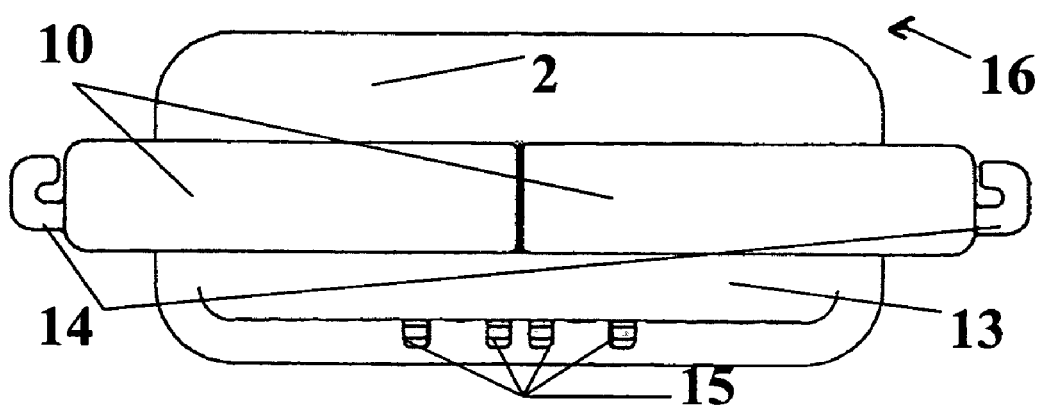
FIG. 6 is a front elevational view of the forehead pad assembly showing the adjustment slots connected to the pad element in the narrowest position of adjustment.

A fully adjustable forehead assembly (16) shown in FIGS. 5 and 6 is customized to fit each patient. In particular, the forehead pad assembly is provided with means for adjusting the locations where the elastic means (11) is connected to opposite ends of the forehead pad. The adjustment, in a direction across the patient's forehead and between opposite sides of the patient's head, provides a custom fit of the appliance to a particular patient. The assembly preferably consists of a forehead pad (2) adapted to contact the patient's forehead and a series of referencing slots (13) designed to receive the pin locks (15) of two bilaterally moveable adjustment blocks (10). Forehead adjustments are accomplished by selecting the best position for the adjustable forehead component pin locks (15) in the desired referencing slots (13). The adjustment is in the location, generally laterally of the patient's head, where the forehead assembly is connected via the elastic bands (11) to the bars (1). The hook of the forehead component (14) should be approximately 3 cm anterior to the hook (19) on the generally vertical wire (1) of the facebow. Alternatively, the foregoing adjustable forehead assembly could be provided by an arrangement wherein instead of having blocks (10) laterally moveable, the hooks (14) themselves could be laterally movable, inwardly and outwardly, to adjust the location of connection to the elastic bands (11).

Elastic elements (11), one on each side of the appliance, each generating approximately 750 gram centimeters, connect the head pad assembly (16) to the hooks (19) on the wire facebow near the area of the temporal bone. This provides the force necessary for treatment.

Figure 7:
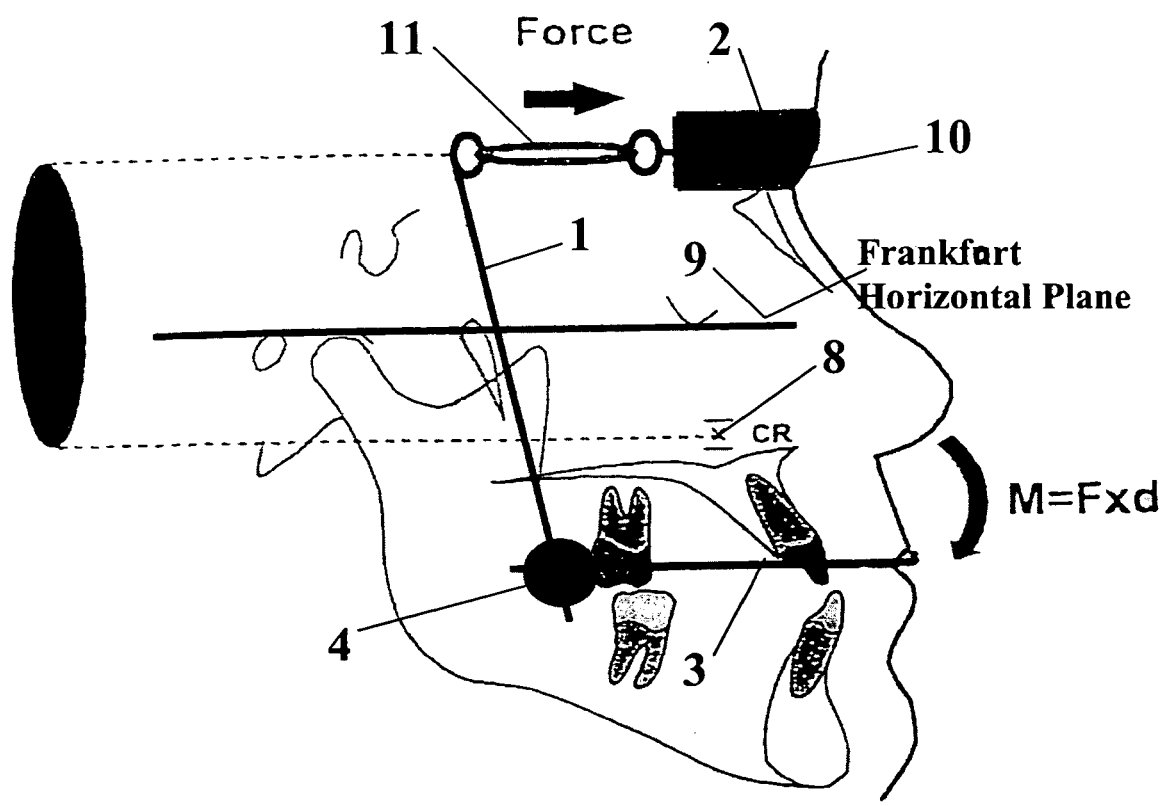
FIG. 7 is an anatomical side view showing the points of attachment of the headgear and associated force and moment vectors.

An important aspect of the appliance involves the direction of force application. The level of force application is positioned above the center of resistance of the maxilla (8) and parallel to the Frankfort horizontal plane (9) as shown in FIG. 7.

It is therefore apparent that the invention accomplishes its intended objectives. While an embodiment of the invention has been described in detail, that is for the purpose of illustration, not limitation.

The invention claimed is:

1. In an orthodontic appliance including a facebow comprising an intra-oral portion adapted for connection to a patient's teeth and an extra-oral portion extending from the intra-oral portion to locations forwardly of both of the patient's ears, a forehead pad serving as the sole means of support for the appliance, and elastic means connected to opposite ends of the forehead pad and to the locations on the extra-oral facebow portion for applying force above the center of resistance of maxilla to rotate the maxilla with downward and backward direction in Class III patients with overbite, the improvement comprising:

forehead pad adjusting means for adjusting the locations where the elastic means is connected to opposite ends of the forehead pad to custom fit the appliance to a particular patient.

2. The orthodontic appliance according to claim 1, wherein the intra-oral facebow portion extends generally horizontally outwardly from where it is adapted for connection to the patient's teeth and wherein the extra-oral facebow portion has a first section extending generally horizontally and rearwardly from the intra-oral facebow portion and a second section extending generally vertically and forwardly of the patient's ears and terminating at locations at the general level of the patient's forehead, wherein the improvement further comprises means for adjusting at least one of the first and second sections.

3. The orthodontic appliance according to claim 2, wherein the improvement further comprises means for adjusting both of the first and second sections.

4. The orthodontic appliance according to claim 2, wherein the first and second sections are each received in a component including means for adjusting at least one of the sections.

5. The orthodontic appliance according to claim 4, wherein the component includes means for adjusting both of the sections.

6. The orthodontic appliance according to claim 1, wherein the forehead pad adjusting means comprises a pair of bilateral adjustment members movable to selected locations in directions across the patient's forehead between opposite sides of the patient's head.

7. In an orthodontic appliance including a facebow comprising an intra-oral portion for connection to components adapted to be secured to a patient's teeth and extending from the patient's mouth where it joins an extra-oral facebow portion having a pair of spaced-apart sections each extending along opposite sides of the patient's face to ends located forwardly of the patient's ears and at the general level of the patient's forehead, a forehead pad having opposite ends and serving as the sole means for providing anchorage for the appliance, and a pair of elastic members each connected to a corresponding one of the ends of the extra-oral facebow sections and the ends of the forehead pad for applying force above the center of resistance of maxilla to rotate the maxilla with downward and backward direction in Class III patients with overbite, the improvement comprising:

a) each of the sections of the extra-oral facebow portion having a first part extending generally horizontally and rearwardly relative to the patient's teeth and a second part extending generally vertically from the first part to the end at the general level of the patient's forehead; and b) the first and second parts each being received in a component including means for adjusting at least one of the parts to custom fit the appliance to a particular patient.

8. The orthodontic appliance according to claim 7, wherein the component includes means for adjusting both of the parts.

9. The orthodontic appliance according to claim 7, wherein the improvement further comprises forehead pad adjusting means for adjusting the locations where the elastic means is connected to opposite ends of the forehead pad to custom fit the appliance to a particular patient.

10. The orthodontic appliance according to claim 9, wherein the forehead pad adjusting means comprises a pair of bilateral adjustment members movable to selected locations in directions across the patient's forehead.

11. In a method for correcting anterior openbite in Class III patients using an orthodontic appliance having a facebow comprising an intra-oral portion for connection to a patient's teeth and an extra-oral portion extending from the intra-oral portion to locations forwardly of both of the patient's ears, a forehead pad serving as the sole means of support for the appliance and elastic means connected to opposite ends of the forehead pad and to the extra-oral facebow portion, the method comprising providing a stationary support by contacting only the cranial portion of a patient's head so that pressure is not exerted against the lower jaw and mandible and applying force in a forward direction toward the patient's forehead and at the forehead level to rotate the maxilla with downward and backward direction in Class III patients with overbite, the force being applied above the center of resistance of maxilla and the direction of the force being substantially parallel to the Frankfort plane, the improvement comprising:

providing an adjustment in the locations where the elastic means is connected to the forehead pad to custom fit the appliance to a particular patient.

12. The method according to claim 11, wherein the improvement further comprises also providing adjustments in the extra-oral portion of the facebow.

13. In an orthodontic appliance comprising a facebow having an intra-oral portion adapted for connection to a patient's teeth and an extra-oral portion extending from the intra-oral portion to locations on opposite sides of the patient's head, a forehead rest serving as the sole means of support for the appliance and elastic means connected to opposite ends of the forehead rest and to the extra-oral facebow portion, the improvement comprising:

an adjustment mechanism in the forehead rest for adjusting the locations where the elastic means is connected to opposite sides of the forehead rest to custom fit the appliance to a particular patient.

14. The orthodontic appliance according to claim 13, wherein the forehead rest comprises a forehead pad for contacting the patient's forehead and a pair of adjustment members each connected to the elastic means and each being selectively connected to the forehead pad at selected locations therealong in directions across the patient's forehead between opposite sides of the patient's head.

15. The orthodontic appliance according to claim 13, wherein another adjustment mechanism also is provided in the extra-oral portion of the facebow.

16. The orthodontic appliance according to claim 15, wherein the extra-oral portion of the facebow has a pair of spaced-apart sections extending along opposite sides of the patient's face, wherein each of the sections of the extra-oral facebow portion has a first part extending generally horizontally and rear-wardly relative to the patient's teeth and a second part extending generally vertically from the first part and wherein the another adjustment mechanism provides for an adjustment of at least one of the first and second parts.

17. The orthodontic appliance according to claim 16, wherein the first and second parts are received in the another adjustment mechanism and wherein the mechanism includes means for adjusting the position of at least one of the parts in the mechanism.

18. The orthodontic appliance according to claim 15, wherein the forehead rest comprises a forehead pad for contacting the patient's forehead and a pair of adjustment members each connected to the elastic means and each being selectively connected to the forehead pad at selected locations therealong in directions across the patient's forehead between opposite sides of the patient's head and where the extra-oral portion of the facebow has a pair of spaced-apart sections extending along opposite sides of the patient's face, wherein each of the sections of the extra-oral facebow portion has a first part extending generally horizontally and rear-wardly relative to the patient's teeth and a second part extending generally vertically from the first part and wherein the adjustment mechanism provides for an adjustment of at least one of the first and second parts.

19. The orthodontic appliance according to claim 18, wherein the first and second parts are received in the adjustment mechanism and wherein the mechanism includes means for adjusting the position of at least one of the parts in the mechanism.

20. The orthodontic appliance according to claim 19, wherein the mechanism includes means for adjusting the positions of both of the parts in the mechanism.

* * * * *